(12) United States Patent
Wicker et al.

(10) Patent No.: US 11,944,678 B2
(45) Date of Patent: Apr. 2, 2024

(54) SYSTEMS AND METHODS FOR TARGETED MASS INOCULATION

(71) Applicant: Ending Patient Zero, LLC, Ponte Vedra Beach, FL (US)

(72) Inventors: Sarah Rose Wicker, Ponte Vedra Beach, FL (US); Mary Kathryn Reynolds, Ponte Vedra Beach, FL (US)

(73) Assignee: Ending Patient Zero, LLC, Ponte Vedra Beach, FL (US)

( * ) Notice: Subject to any disclaimer, the term of this patent is extended or adjusted under 35 U.S.C. 154(b) by 0 days.

(21) Appl. No.: 18/125,069

(22) Filed: Mar. 22, 2023

(65) Prior Publication Data

US 2023/0321214 A1    Oct. 12, 2023

Related U.S. Application Data

(60) Provisional application No. 63/322,700, filed on Mar. 23, 2022.

(51) Int. Cl.

| | | |
|---|---|---|
| *A61K 38/16* | (2006.01) | |
| *A61K 38/19* | (2006.01) | |
| *A61K 39/00* | (2006.01) | |
| *A61K 39/12* | (2006.01) | |
| *C12N 5/10* | (2006.01) | |
| *C12N 15/63* | (2006.01) | |

(52) U.S. Cl.
CPC .................................. *A61K 39/12* (2013.01)

(58) Field of Classification Search
CPC .......... A61K 39/39; A61K 2039/55516; A61K 39/395; A61K 2039/54; A61K 2039/55
See application file for complete search history.

(56) References Cited

U.S. PATENT DOCUMENTS 8,967,029 B1 *    3/2015    Calvert .................... B64D 1/02
239/8

* cited by examiner

*Primary Examiner* — Barry A Chestnut
(74) *Attorney, Agent, or Firm* — Camille A. Wilson; Wilson Dutra, PLLC

(57) ABSTRACT

The present disclosure provides for systems and methods for targeted mass inoculation. A transmission system for targeted mass inoculation may comprise a first pathogen, wherein first pathogen may comprise a vaccination for an infectious disease. The transmission system may comprise a host that receives the first pathogen. The transmission system may comprise a vector that receives a second pathogen from the host. The second pathogen may inoculate a secondary host when the secondary host receives the second pathogen from the vector. The vector may comprise a mechanical device. When the vector comprises a mechanical device, the vector may comprise a computing device. The computing device may identify a suitable secondary host. The computing device may comprise an algorithm for secondary host recognition and differentiation. The computing device may retain a database comprising indicators of which secondary host candidates have already received the pathogen.

12 Claims, 8 Drawing Sheets

```
┌─────────────────────┐
│ ADMINISTER A FIRST  │
│ PATHOGEN TO AT LEAST│
│     ONE HOST        │
│                 705 │
└──────────┬──────────┘
           │
           ▼
┌─────────────────────┐
│  INTRODUCE A VECTOR │
│     TO THE HOST     │
│                 710 │
└──────────┬──────────┘
           │
           ▼
┌─────────────────────┐
│ INTRODUCE VECTOR TO │
│   SECONDARY HOST    │
│                 720 │
└─────────────────────┘
```

```
┌─────────────────────┐
│ INJECT A HOST WITH A│
│      PATHOGEN       │
│                 805 │
└──────────┬──────────┘
           ▼
┌─────────────────────┐
│ INTRODUCE A VECTOR TO│
│      THE HOST       │
│                 810 │
└──────────┬──────────┘
           ▼
┌─────────────────────┐
│ TRANSFER PATHOGEN TO│
│  VECTOR FROM HOST   │
│                 815 │
└──────────┬──────────┘
           ▼
┌─────────────────────┐
│ INTRODUCE VECTOR TO │
│   SECONDARY HOST    │
│                 820 │
└──────────┬──────────┘
           ▼
```

- 805 INJECT A HOST WITH A PATHOGEN
- 810 INTRODUCE A VECTOR TO THE HOST
- 815 TRANSFER PATHOGEN TO VECTOR FROM HOST
- 820 INTRODUCE VECTOR TO SECONDARY HOST
- 825 HAS SECONDARY HOST RECEIVED PATHOGEN?
- 830 (YES) VECTOR SELECTS ANOTHER SECONDARY HOST
- 835 (NO) INSERT PATHOGEN INTO SECONDARY HOST VIA THE VECTOR

FIG. 8

SYSTEMS AND METHODS FOR TARGETED MASS INOCULATION

BACKGROUND

Traditionally, mankind has faced the challenge of infectious disease since inception. Archaeological studies have shown that even 4,000 years ago, people attempted to fight against infection with every resource available. Unfortunately, even today, the causative agents of diseases, including viruses, parasites, bacteria, and fungi, have extraordinarily varied life cycles and modes of transmission. These diseases have the ability to adapt and persist not only in humans, but other animal species as well.

Many disease-causing agents have silent transmission cycles involving wild animals that co-evolve with the infectious agent and exhibit no signs of disease. Some diseases occur when a causative agent harbored by a wild animal jumps species to domesticated animals and thence to humans. Others are primarily diseases of domesticated animal species. Humans may be infected by direct contact with wild or domesticated animals, or indirectly by ingestion of contaminated milk or meat, inhalation of aerosolized secretions or excrement, or by being bitten by insects or ticks.

Despite this complexity of epidemiological patterns, the opportunities for intervention often boil down to a few simple bottlenecks in the disease transmission process. For example, milk-borne diseases can be prevented by pasteurization, certain meat-borne diseases by inspection and animal husbandry improvements, and other diseases avoided by limiting contact with known high-risk species.

Where the risk of infection is high, or the resulting disease severe, vaccines may be the most efficient and cost-effective means of disease prevention and control. Alternative methods for control of diseases have generally employed trapping, poisoning, or other means of destroying the offending animal vector, however, these methods have mixed (and often negative) records of success and are becoming socially unacceptable.

Vaccines have taken many forms to become effective at disease prevention. In addition to human vaccination, animals that are traditional hosts for diseases have also been immunized. Different methods of immunization have been explored in efforts to effectuate widespread immunization quickly. For example, to increase the rate of dissemination, carriers such as mosquitoes have been investigated as potential vaccine distributors. However, using an autonomous, living organism to vaccinate others present numerous ethical and practical problems that render it an unfeasible alternative.

One challenge with using carriers is controlling the number of vaccinations each animal or person would receive. For instance, one study placed several mice in a container with mosquitoes carrying a vaccine and discovered the number of bites each mouse received varied greatly. Such a large variation in the number of mosquito bites results in vastly different doses of the vaccine being administered. To illustrate this conundrum, it would be similar to administering one dose of a measles vaccine to some people while administering 500 doses to others. Additionally, the use of mosquitoes to vaccinate people would inevitably result in vaccinating at least some people without their informed consent.

SUMMARY OF THE DISCLOSURE

What is needed are systems and methods for targeted mass inoculation. Such systems and methods may provide for efficient and effective ways of preventing the spread of one or more diseases in a variety of populations, such as human, animal, and insect. In some aspects, systems and methods for targeted mass inoculation may comprise one or more of a plurality of different vectors to aid in the distribution of at least one pathogen. When a vector includes a live organism, such as a mosquito, a method is needed to overcome dosage distribution issues and ensure the pathogen is administered to an intended secondary host.

The present disclosure provides for systems and methods for targeted mass inoculation. In some embodiments, a transmission system for targeted mass inoculation may comprise a first pathogen and a second pathogen. In some implementations, the first pathogen may comprise a vaccination for an infectious disease. In some implementations, the second pathogen may comprise one or more antibodies. In some aspects, the transmission system may comprise at least one host that receives the first pathogen. In some embodiments, the transmission system may comprise at least one vector that receives the second pathogen from the host. In some implementations, the second pathogen may inoculate a secondary host when the secondary host receives the second pathogen from the vector. In some aspects, at least one portion of the first pathogen may be at least partially different from at least one portion of the second pathogen. In some non-limiting exemplary embodiments, the first pathogen may be the same as the second pathogen.

In some aspects, the vector may comprise at least one mechanical device. In some implementations, a vector that comprises a mechanical device may be configured to deliver at least one of: a first pathogen and a second pathogen to a secondary host. In some embodiments, when the vector comprises a mechanical device, the vector may further comprise at least one computing device. In some implementations, the computing device may identify at least one suitable secondary host. In some aspects, the computing device may comprise at least one algorithm for facilitating secondary host recognition and differentiation by the computing device. In some implementations, the computing device may retain or be communicatively coupled to at least one database comprising one or more indicators of which secondary host candidates have already received the first or second pathogen.

BRIEF DESCRIPTION OF THE DRAWINGS

The accompanying drawings that are incorporated in and constitute a part of this specification illustrate several embodiments of the disclosure and, together with the description, serve to explain the principles of the disclosure:

FIG. 3 illustrates an exemplary transmission system comprising immunization, according to some embodiments of the present disclosure.

FIG. 7 illustrates exemplary method steps for a process for targeted mass inoculation using a transmission system, according to some embodiments of the present disclosure.

FIG. 8 illustrates exemplary method steps for a process for targeted mass inoculation using a transmission system, according to some embodiments of the present disclosure.

DETAILED DESCRIPTION

Figure 1:
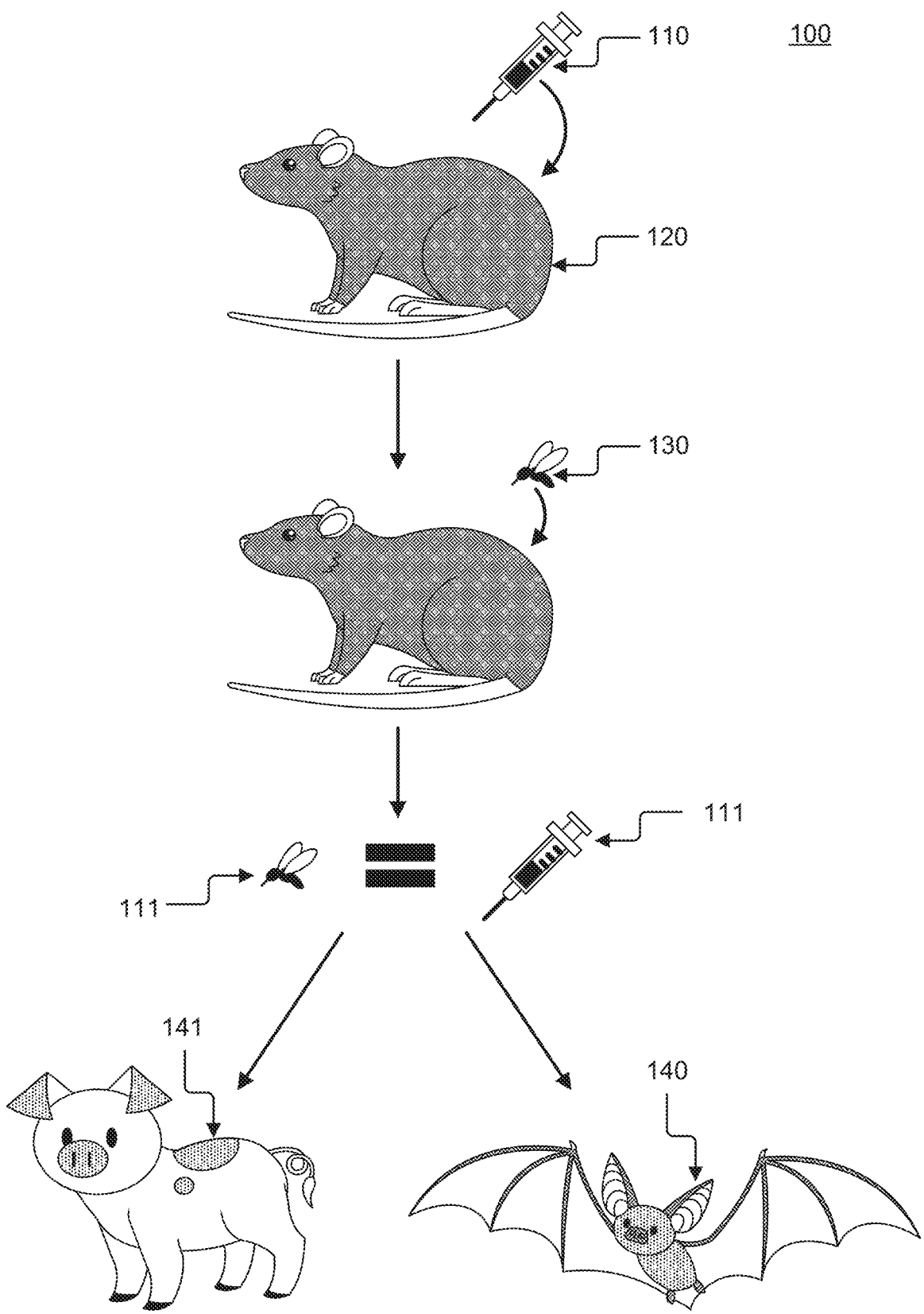
FIG. 1 illustrates an exemplary transmission system, according to some embodiments of the present disclosure.

The present disclosure provides for systems and methods for targeted mass inoculation. In some embodiments, the transmission system may comprise a first at least one pathogen and a second at least one pathogen. In some implementations, the first pathogen may at least partially comprise at least one vaccination for at least one infectious disease. In some implementations, the second pathogen may at least partially comprise one or more antibodies. In some aspects, the transmission system may comprise at least one host that receives the first pathogen. In some embodiments, the transmission system may comprise at least one vector that receives the second pathogen from the host. In some implementations, the second pathogen may inoculate a secondary host when the secondary host receives the second pathogen from the vector. In some aspects, at least one portion of the first pathogen may be at least partially different from at least one portion of the second pathogen. In some non-limiting exemplary embodiments, the first pathogen may be the same as the second pathogen.

According to some aspects of the present disclosure, mass inoculation through the prescribed methods and systems may facilitate safe administration of a first or second pathogen to a plurality of targeted secondary hosts that may prevent subsequent human or animal contraction of one or more infectious diseases.

In the following sections, detailed descriptions of examples and methods of the disclosure will be given. The descriptions of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Vector: as used herein, refers to a carrier of at least one pathogen. In some embodiments, a vector may comprise at least one living organism that delivers the pathogen to at least one intended secondary host upon contracting the pathogen from contact with at least one infected host. In some implementations, a vector may comprise at least one mechanical device that administers the pathogen to a secondary host based on one or more instructions or directions received from embedded software and at least one associated algorithm.

Pathogen: as used herein, refers to an infectious disease, malady, or one or more agents or elements associated therewith. In some aspects, a pathogen may comprise one or more living or dead components. In some embodiments, a pathogen may comprise one or more antibodies. In some implementations, a pathogen may comprise at least one vaccine. In some aspects, a pathogen may comprise a hybrid disease that may further comprise one or more viruses, parasites, bacteria, or fungi, as non-limiting examples, as well as any combination thereof. In some embodiments, a hybrid disease may enable a secondary host to develop one or more antibodies to a second disease based on one or more causative agents of the second disease having a similar structural composition to other previously-administered vaccines.

Host: as used herein, refers to any entity configured to receive at least one pathogen via external administration.

Secondary host: as used herein, refers to a second host who receives at least one pathogen from at least one vector. This is opposed to an original host, which may contract a pathogen via external administration. In some embodiments, a secondary host may comprise at least one intermediary animal that frequently stores viral strains without suffering symptoms. In some aspects, a pathogen may be transmitted to a secondary host to prevent the contraction and subsequent transmission or mutation of one or more diseases. By preventing a secondary host from contracting the pathogen via immunity, subsequent infection of humans through contact, consumption, or other interaction with the secondary host may be substantially prevented.

Referring now to FIG. 1, an exemplary transmission system 100, according to some embodiments of the present disclosure, is illustrated. In some embodiments, the transmission system 100 may comprise a first at least one pathogen 110. In some implementations, the transmission system 100 may comprise at least one host 120. By way of example and not limitation, a host 120 may comprise a living organism, such as an insect, animal, or human. In some embodiments, the host 120 may contract the first pathogen 110. In some aspects, the contraction of the first pathogen 110 may occur via one or more methods, such as injection or ingestion, as non-limiting examples. In some aspects, at least one vector 130 may receive a second at least one pathogen 111 from the host 120. In some embodiments, the vector 130 may transfer the second pathogen 111 to at least one secondary host 140, 141. By way of example and not limitation, a secondary host 140, 141 may comprise at least one living organism, such as a human, animal, or insect.

In some implementations, the first pathogen 110 may at least partially comprise at least one vaccine. In some aspects, the vaccine may comprise one or more portions of the first pathogen 110 that may be insufficient to adversely affect the host 120, but sufficient for the host 120 to develop or produce one or more antibodies to the first pathogen 110. In some embodiments, the vector 130 may receive a second pathogen 111 from the host 120. In some aspects, the second pathogen 111 may at least partially comprise the antibodies developed by the host 120 in reaction to the first pathogen 110. In some implementations, the vector 130 may deliver the second pathogen 111 to at least one secondary host 140, 141.

In some aspects, the secondary host 140, 141 may receive the second pathogen 111 from the vector 130 via digestion or ingestion. For example, a fly or mosquito, acting as a vector 130, may carry the second pathogen 111 and, upon being eaten by a bat, acting as a secondary host, the bat may contract the second pathogen 111 via digestion. In some embodiments, the secondary host 140 may receive the second pathogen 111 from the vector 130 when the vector 130 interacts with the secondary host 140, such as when a mosquito bites a secondary host 140, 141.

By using the vector 130 to distribute the second pathogen 111 to a secondary host 140, the vector 130 may introduce the secondary host to a non-lethal dose of the second pathogen 111. In some aspects, this may allow a secondary host 140, 141 to develop one or more antibodies to the second pathogen 111 without the risk of developing symptoms in reaction to the second pathogen 111. Because the vector 130 is used to distribute the second pathogen 111 to an animal secondary host 140, 141, there may be no need for consent that may be required to inoculate humans.

In some implementations, the second pathogen 111 may comprise sufficient strength to make the secondary host 140, 141 resistant to the second pathogen 111, but not of sufficient potency to cause harm to the secondary host 140, 141 if the secondary host 140, 141 receives more than one dosage of the second pathogen 111, such as when more than one mosquito may bite the same pig, as a non-limiting example. In some embodiments, the vector 130 may comprise at least one genetic modification sufficient to render the vector 130 unable to reproduce, thereby facilitating at least partial control over distribution of the second pathogen 111.

In some aspects, the first pathogen 110 may comprise a hybrid bacterium or virus that utilizes traditional infiltration methods to enter a body and provide immunization. As an illustrative example, this hybrid formation may involve replacing the gene encoding the yellow fever vaccine virus' envelope protein with the corresponding gene of West Nile virus. The hybridization process may comprise replacing the gene encoding the yellow fever vaccine virus' envelope (E) protein with the corresponding gene of West Nile virus. The hybrid formation with the E gene may comprise a plurality of attenuating mutations because of the hybridization.

This hybrid vaccine may enable a host-restricted vaccine to adapt to a secondary host 140, 141. In some aspects, a secondary host 140, 141 inoculated with the hybrid vaccine may develop one or more neutralizing antibodies against West Nile and become protected against future severe intrathecal challenges that may manifest as a result of a West Nile virus infection.

Figure 2:
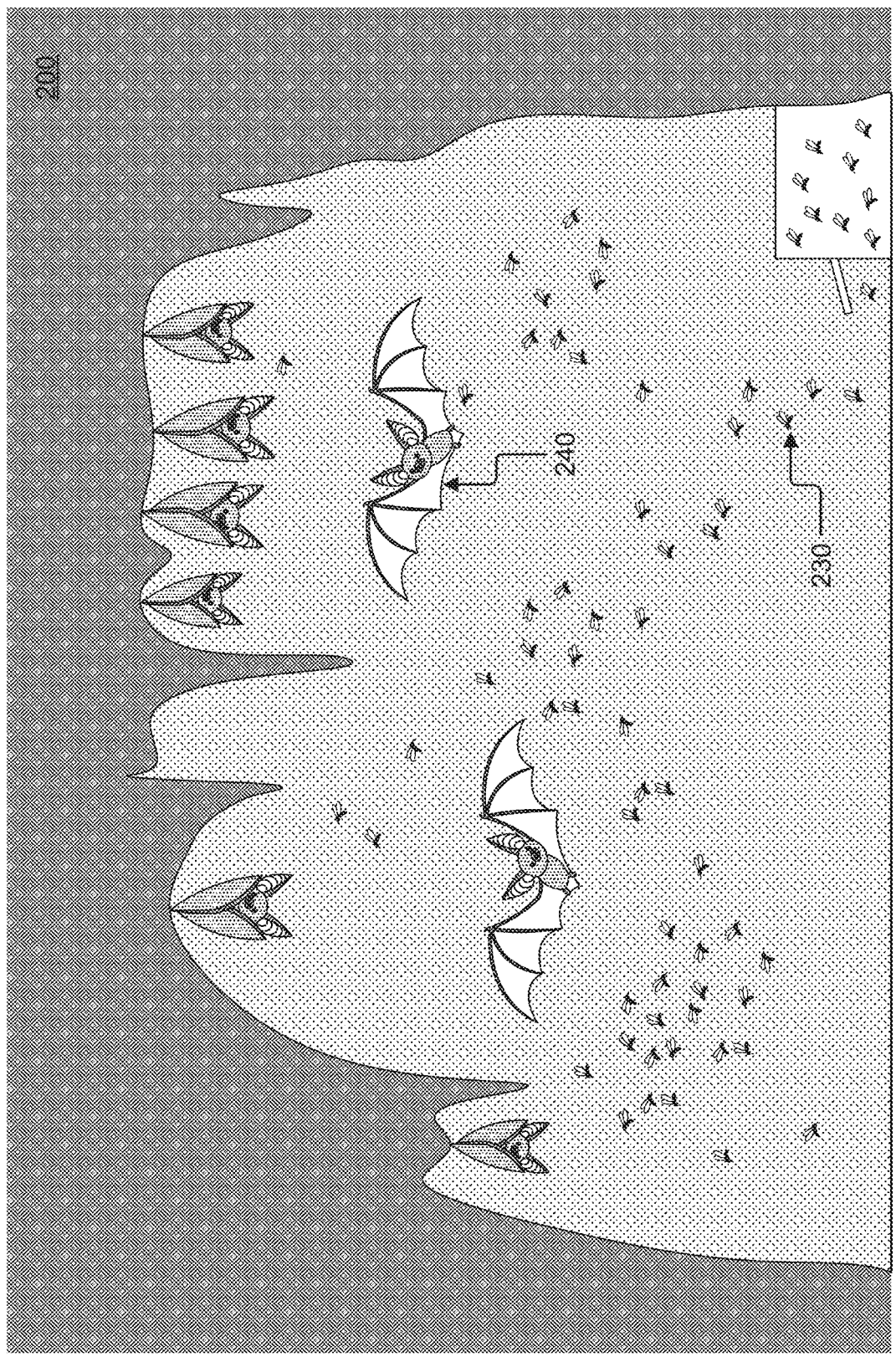
FIG. 2 illustrates an exemplary transmission system, according to some embodiments of the present disclosure.

Referring now to FIG. 2, an exemplary transmission system 200, according to some embodiments of the present disclosure, is illustrated. In some embodiments, the transmission system 200 may comprise a plurality of vectors 230. In some implementations, the vectors 230 may interface with a plurality of secondary hosts 240, wherein the interfacing may comprise the vectors 230 physically contacting the secondary hosts 240, such as, for example and not limitation, by biting the secondary hosts 240 or by being consumed by the secondary hosts 240.

In some aspects, the vectors 230 may transfer at least one pathogen to the secondary hosts 240. In some embodiments, the pathogen may allow the secondary hosts 240 to form one or more antibodies that may make the secondary hosts 240 resistant to future contraction of the pathogen. In some implementations, the vectors 230 may be released in a concentrated or confined area to provide intentional interaction with the intended secondary hosts 240. In some aspects, the vectors 230 may be released in accordance with one or more predetermined factors, such as time, date, season, weather conditions, or any other factor(s) that may potentially facilitate the interaction between the vectors 230 and the secondary hosts 240.

As an illustrative example, a group of non-reproductive mosquitos may be released at or near the entrance of a cavern that a large population of bats are known to inhabit. A concentrated number of mosquitoes in a confined area may minimize or prevent any accidental interaction and infection of other unintended hosts by the mosquitos. In some aspects, the mosquitos may carry at least one pathogen contracted from at least one previous animal that may spread to the bats upon contact. In some embodiments, the mosquitos may be live bait that distribute the pathogen to the bats upon digestion.

In some implementations, the pathogen may be transferred as the mosquitoes bite the bats. In some aspects, the pathogen may be nonlethal to the bats. In some implementations, the bats may, upon contracting the pathogen, develop or produce one or more antibodies to the contracted pathogen. These antibodies may allow the bats to resist future contraction of the same pathogen. Even though the pathogen may be harmless to the bats, the resistance of the bats to the pathogen may prevent the pathogen from being passed onto creatures that may have future interactions with the bats, such as humans. In some aspects, humans may be more susceptible to the pathogen, and by nature of the bat's resistance, humans may not contract a pathogen that may normally be transferred to humans via direct contact with bats.

Figure 3:
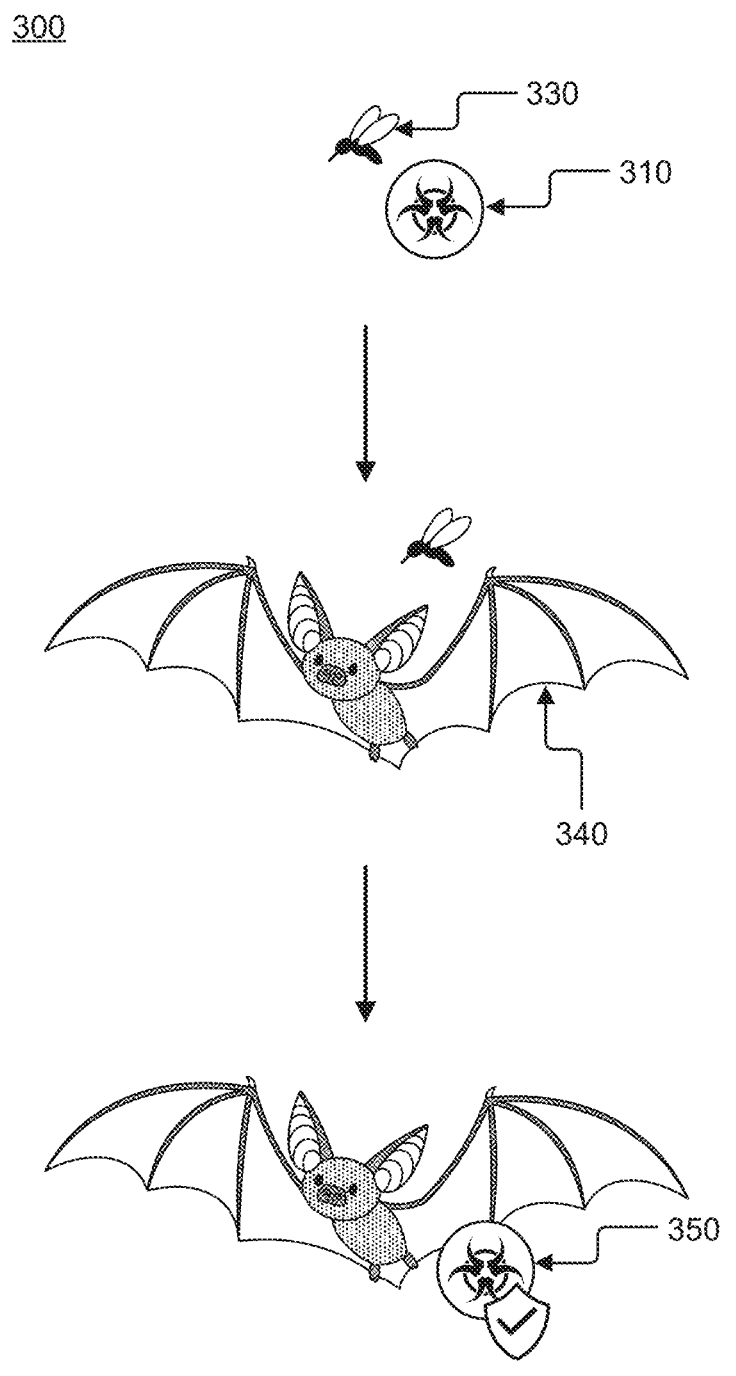

Referring now to FIG. 3, an exemplary transmission system 300 comprising immunization, according to some embodiments of the present disclosure, is illustrated. In some embodiments, at least one vector 330 may transfer at least one pathogen 310 to at least one secondary host 340. In some implementations, the pathogen 310 may provide the secondary host with immunization 350.

In some aspects, the pathogen 310 may comprise at least one hybrid bacterium or virus that utilizes traditional infiltration methods to enter a body and provide immunization 350. As an illustrative example, because the West Nile virus and the Yakose virus may be both of the Flavivirus genus, an existing yellow fever vaccine, or one similar to it, may be incorporated into the development of a Yakose vaccine. This hybrid formation may involve replacing the gene encoding the yellow fever vaccine virus' envelope protein with the corresponding gene of the Yakose virus.

This hybrid vaccine may enable a host-restricted vaccine to adapt to a secondary host 340. In some aspects, a secondary host 340 inoculated with the hybrid vaccine may develop one or more neutralizing antibodies against the Yakose virus and thereby become protected against future severe intrathecal challenges.

Figure 4A:
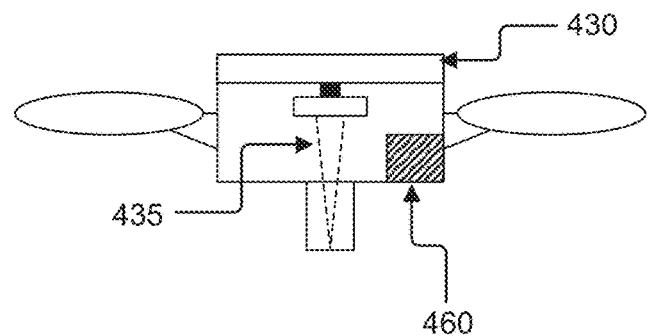
FIG. 4A illustrates an exemplary transmission system, according to some embodiments of the present disclosure.
Figure 4B:
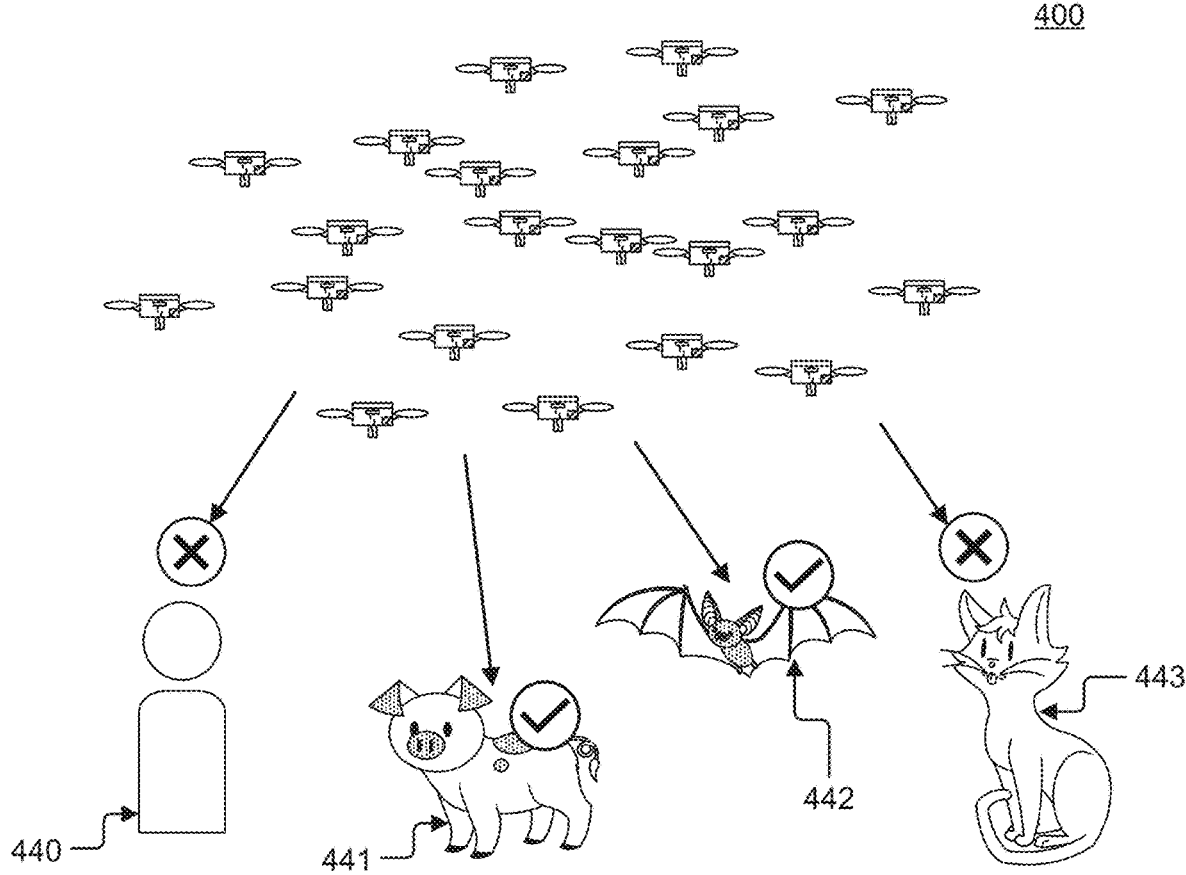
FIG. 4B illustrates an exemplary transmission system, according to some embodiments of the present disclosure.

Referring now to FIGS. 4A-B, an exemplary transmission system 400, according to some embodiments of the present disclosure, is illustrated. In some embodiments, the transmission system 400 may comprise at least one vector 430. In some aspects, the vector 430 may comprise at least one mechanical device, such as, by way of example and not limitation, an unmanned vehicle, which may be aerial, terrestrial, or aquatic. In some implementations, the vector 430 may comprise at least one injection device 435, such as a needle or syringe, as non-limiting examples. In some aspects, the vector 430 may immunize or inoculate at least one preferred, predetermined, or targeted secondary host 441, 442. In some aspects, a preferred secondary host 441, 442 may be determined using one or more predetermined variables that may be associated with secondary hosts 440, 441, 442, 443.

By way of example and not limitation, the predetermined variables may comprise at least one of: an age or age range, gender, ethnicity, prior immunization or previous pathogen reception status, species, or location of the secondary host 440, 441, 442, 443. For example, a vector 430 may be configured to contact a preferred secondary host 441, 442 that comprises a species as well as an age or age range that may be safe for contracting at least one pathogen. In some non-limiting exemplary embodiments, a vector 430 may be configured to contact a preferred secondary host 441, 442 that is an animal, such as a pig or a bat. By way of example and not limitation, a vector 430 may be configured to recognize whether a secondary host 440, 441, 442, 443 is within a predetermined geographical location, such as by utilizing one or more Global Positioning System (GPS) sensors. By way of further example and not limitation, a vector 430 may be configured to recognize whether a secondary host 440, 441, 442, 443 has already received or contracted a pathogen, such as by using one or more infrared sensors that may detect an infrared signature of the secondary host 440, 441, 442, 443, which, in some instances, may be raised or elevated when the secondary host 440, 441, 442, 443 is experiencing an immune response to the pathogen.

In some embodiments, the vector 430 may comprise at least one mechanical device. In some implementations, the vector 430 may comprise at least one computing device 460. In some aspects, the computing device 460 may comprise one or more executable algorithms. In some embodiments, the algorithms may be configured to differentiate between preferred, predetermined, or targeted secondary hosts 441, 442 and restricted secondary hosts 440, 443, wherein the preferred secondary hosts 441, 442 may be determined using one or more predetermined variables. By way of example and not limitation, the predetermined variables may comprise at least one of: an age or age range, gender, ethnicity, prior immunization or previous pathogen reception status, species, or location of the secondary host 440, 441, 442, 443.

In some aspects, the vector 430 may comprise one or more sensors, wherein the sensors may be configured to determine one or more predetermined factors of the secondary hosts 440, 441, 442, 443. By way of example and not limitation, sensors may comprise one or more of: temperature sensors, location sensors, heat sensors, infrared sensors, proximity sensors, motion sensors, light sensors, presence sensors, or sound sensors. In some embodiments, the vector 430 may comprise at least one transmitting device, wherein the transmitting device may be configured to send at least one datum obtained by the sensors to the computing device 460 or to at least one external or remote server. In some implementations, the vector 430 may comprise at least one storage medium, such as, for example and not limitation, a database.

In some implementations, the computing device 460 may be configured to detect, identify, and/or generate one or more differentiation markers to indicate which preferred secondary hosts 441, 442 have previously received or contracted a pathogen. In some embodiments, the differentiation markers may facilitate prevention of multiple injections to preferred secondary hosts 441, 442 that have already received or contracted the pathogen by instructing the computing device 460 to refrain from delivering the pathogen to preferred secondary hosts 441, 442 that have already received the pathogen. In some aspects, the differentiation markers may comprise one or more physical markings or indicators located directly on the preferred secondary hosts 441, 442 or one or more virtual markings that may correspond to one or more identifiers within at least one database. In some implementations, the computing device 460 may be configured with artificial intelligence. In some aspects, the artificial intelligence of the computing device 460 may facilitate detection or identification of the differentiation markers. In some non-limiting exemplary embodiments, a computing device 460 that comprises artificial intelligence may be trained using at least one machine learning process. By way of example and not limitation, a machine learning process for the computing device 460 may comprise iteratively presenting the computing device 460 with different images of one or more preferred hosts 441, 442, some of which comprise one or more differentiation markers, so that the computing device 460 may progressively improve its ability to detect and identify differentiation markers on preferred secondary hosts 441, 442.

In some non-limiting exemplary embodiments, the vector 430 may be configured to apply one or more differentiation markers that comprise physical markings or indicators to a preferred secondary host 441, 442 once the preferred secondary host 441, 442 has received or contracted a pathogen. By way of example and not limitation, the vector 430 may comprise one or more dispensing mechanisms, such as a nozzle, sprayer, or similar applicator that may dispense at least one substance that may be applied to the preferred secondary host 441, 442 after the preferred secondary host 441, 442 receives or contracts a pathogen. As an illustrative example, the vector 430 may dispense a substance in the form of dye or paint that may at least temporarily adhere to at least one external portion of the preferred secondary host 441, 442 to form at least one physical marking such that the marking may be subsequently recognized by the computing device 460 using at least one visual capture device, such as a camera or scanner, so that the computing device 460 may determine that the preferred secondary host 441, 442 has previously received or contracted the pathogen, thereby causing the computing device 460 to refrain from delivering the pathogen to that preferred secondary host 441, 442 in the future. In some aspects, one or more vectors 430 may be configured to apply differentiation markers to a plurality of preferred secondary hosts 441, 442 simultaneously, such as when the plurality of preferred secondary hosts 441, 442 may receive a pathogen contemporaneously, such as during a mass inoculation process that may comprise the dispersion of pathogens in the form of aerosolized vapor, as a non-limiting example.

In some aspects, the vector 430 may apply one or more substances to one or more external portions of a preferred secondary host 441, 442 that may reflect wavelengths of a portion of the electromagnetic spectrum that are not perceivable by the human eye, but that may be detectable by the computing device 460 using one or more sensors, such as, for example and not limitation, an infrared or ultraviolet sensor or an infrared or ultraviolet camera. In some non-limiting exemplary embodiments, the vector 430 may use an injection device 435 to inject a preferred secondary host 441, 442 with one or more substances that may be detectable within the preferred secondary host 441, 442 from outside the preferred secondary host 441, 442 by the computing device 460 using one or more scanning devices, such as those used to perform x-radiation imaging or ultrasonography, as non-limiting examples.

In some non-limiting exemplary embodiments, one or more preferred secondary hosts 441, 442 may be physically tagged or branded when they have received the pathogen, either manually or via the vector 430, or the computing device 460 may identify one or more unique physical characteristics, such as, for example and not limitation, fur or skin patterns or facial features, of preferred secondary hosts 441, 442 that have received the pathogen, wherein the unique characteristics may be stored as identifiers in at least one database or other storage medium and then subsequently referenced to identify the preferred secondary hosts 441, 442 at a later time. In some aspects, the computing device 460 may comprise visual recognition or other identifying software to confirm only intended preferred secondary hosts 441, 442 receive the pathogen.

Figure 5:
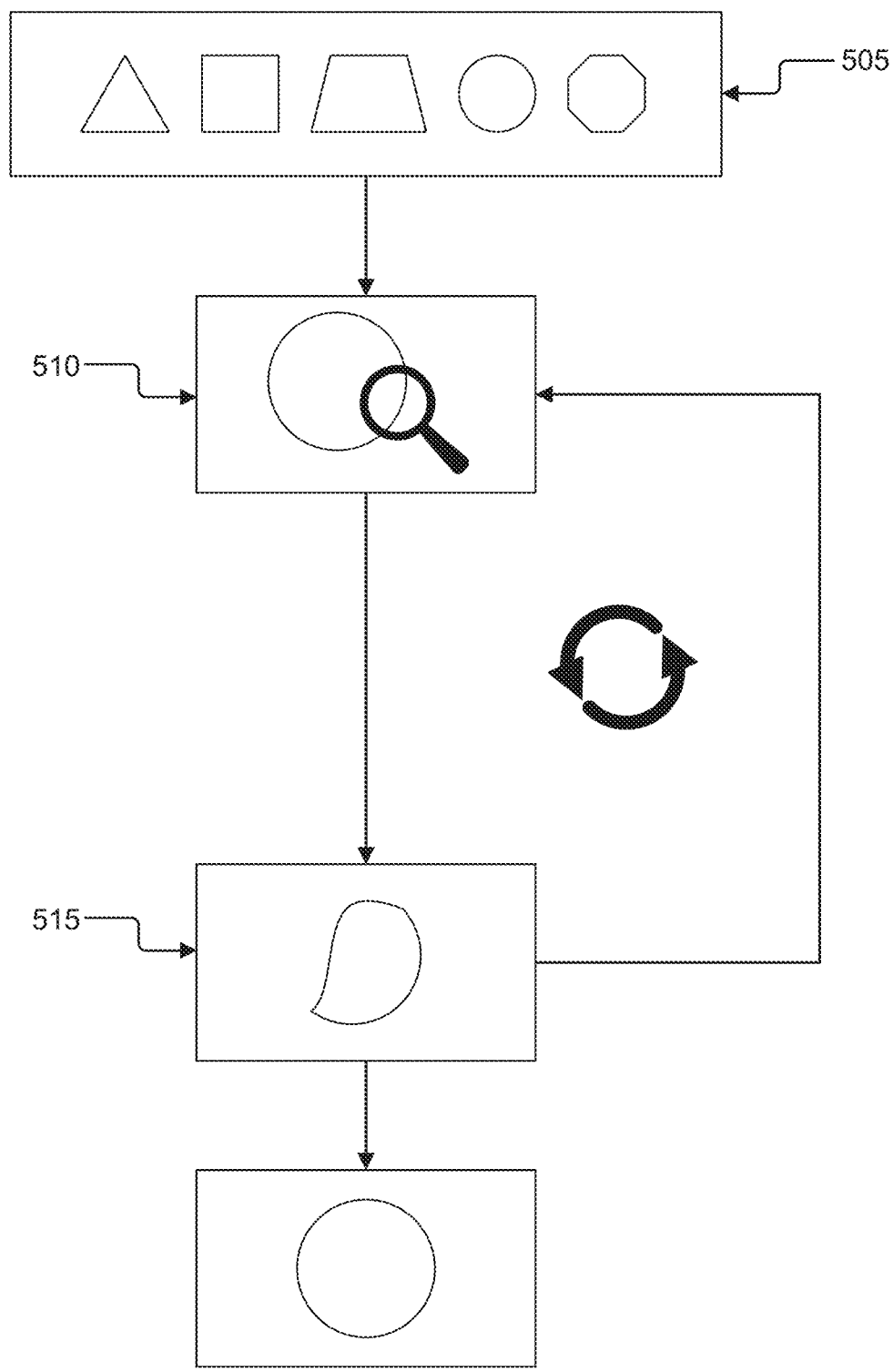
FIG. 5 illustrates an exemplary algorithm, according to some embodiments of the present disclosure.

Referring now to FIG. 5, an exemplary algorithm 570, according to some embodiments of the present disclosure, is illustrated. In some embodiments, the algorithm 570 may receive a plurality of predetermined variables 505. In some implementations, the algorithm 570 may group predetermined variables 505 by one or more predefined rules, associations, or attributes, as a non-limiting list.

In some embodiments, the algorithm 570 may receive a plurality of predetermined variables 505. In some aspects, the algorithm 570 may comprise machine learning. In some implementations, the algorithm 570 may utilize machine learning to reference the predetermined variables 505 for comparison 510 to at least one submitted identification. In some aspects, the algorithm 570 may utilize one or more identified attributes associated with the predetermined variables 505 to classify the submitted identification. In some embodiments, the algorithm 570 may use machine learning to provide a ranking of similarity between the submitted identification and the received predetermined variables 505. In some implementations, the algorithm 570 may classify the submitted identification and associate the submitted identification with one or more of the predetermined variables 505.

As an illustrative example, the algorithm 570 may receive one or more images of a pig for the purpose of visual recognition of pigs. The pictures of pigs may comprise pigs with various skin colors and patterns. The algorithm 570 may use the colors, patterns, and other non-limiting variables common among the pictures of pigs to further categorize future visually inspected pigs.

In some aspects, the algorithm 570 may use identified attributes to classify an animal. For example, the algorithm 570 may notice that an animal comprises a relatively small size and has a body, a head with pointed ears, four legs, a long tail, and fur. Without additional facts, the algorithm 570 may use the combination of identified attributes of the observed animal to conclude that the animal is a cat. In some implementations, the algorithm 570 may indicate a low association between the submitted identification and the received predetermined variables 505, thereby indicating that the cat is not likely to be a pig. In some aspects, the algorithm 570 may use a submitted identification to generate one or more new predetermined variables 515.

In some embodiments, the algorithm 570 may comprise one or more recursive functions that may improve accurate identification over time. In some implementations, the algorithm 570 may quantify accurate identification by a predetermined threshold of acceptance or accuracy. In some aspects, the algorithm 570 may improve over time by using the data collected and categorized from previous animals to improve the algorithm's likelihood for correctly identifying animals in the future.

Figure 6:
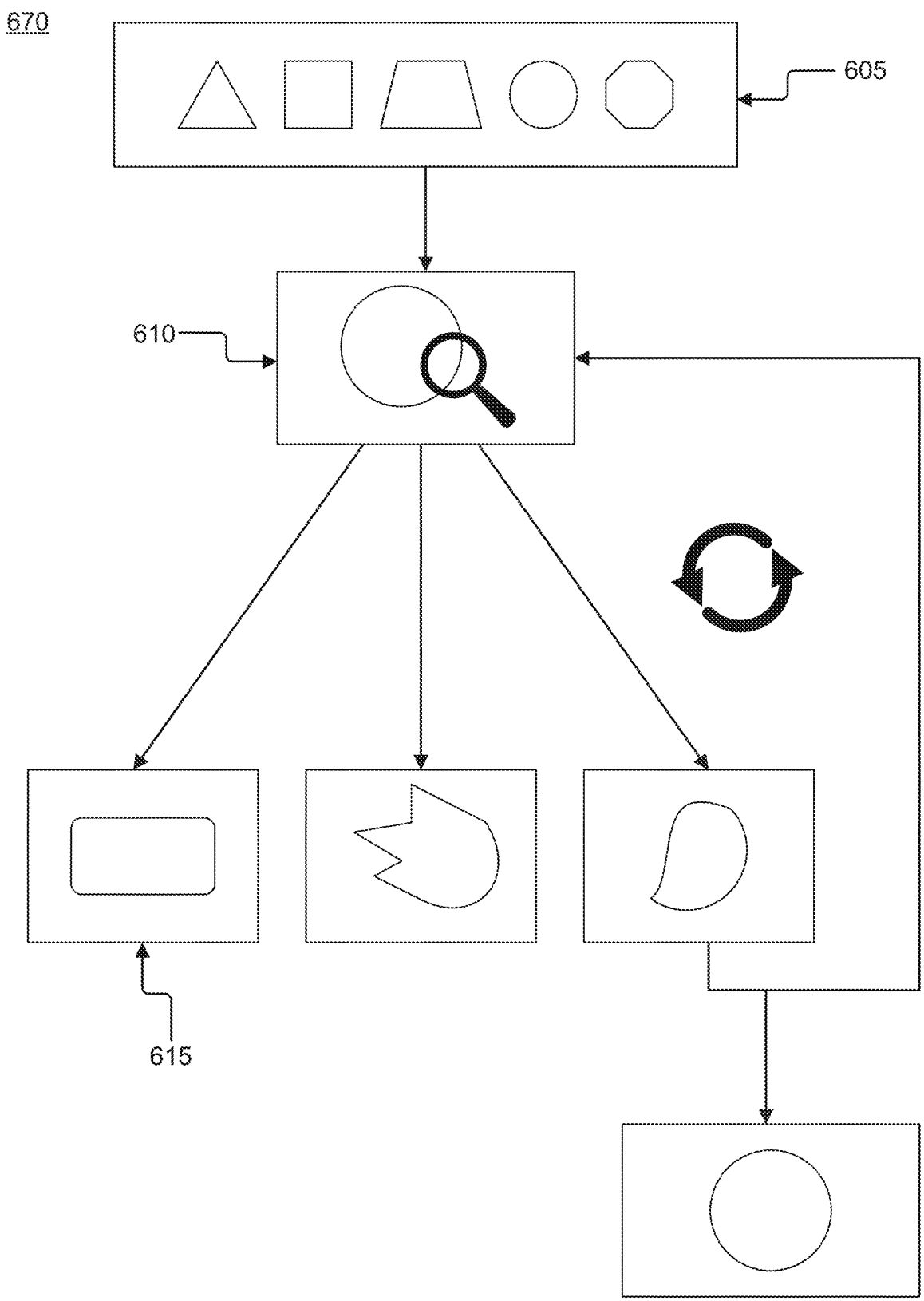
FIG. 6 illustrates an exemplary algorithm, according to some embodiments of the present disclosure.

Referring now to FIG. 6, an exemplary algorithm 670, according to some embodiments of the present disclosure, is illustrated. In some embodiments, the algorithm 670 may receive a plurality of predetermined variables 605. In some implementations, the algorithm 670 may reference the predetermined variables 605 for comparison 610 to a submitted identification. In some aspects, the algorithm 670 may utilize one or more identified attributes associated with the predetermined variables 605 to classify the submitted identification.

In some embodiments, the algorithm 670 may provide a ranking of similarity between the submitted identification and the received predetermined variables 605. In some implementations, the algorithm 670 may classify the submitted identification and associate the submitted identification with one or more of the predetermined variables 605. In some embodiments, the algorithm 670 may provide one or more classifications for a submitted identification that may associate the submitted identification with two or more of the predetermined variables 605. In some aspects, the algorithm 670 may produce classifications for two or more submitted identifications simultaneously.

In some implementations, the algorithm 670 may indicate a low association between the submitted identification and the received predetermined variables 605. In some aspects, the algorithm 670 may use a submitted identification to generate one or more new predetermined variables 615. In some embodiments, the algorithm 670 may refine new predetermined variables 615 recursively based on feedback from subsequently submitted identifications. In some implementations, new predetermined variables 615 may become distinct from other received predetermined variables via recursion of the algorithm 670.

Referring now to FIG. 7, exemplary method steps for a process 700 for targeted mass inoculation using a transmission system, according to some embodiments of the present disclosure, are illustrated. In some aspects, at 705, the process 700 may comprise administering a first at least one pathogen to at least one host. In some embodiments, the first pathogen may be transmitted to the host via injection, aerosolized vapor, or consumption, as non-limiting examples of pathogen transmission. In some implementations, at 710, at least one vector may be introduced to the host, wherein the introduction may facilitate transfer of a second at least one pathogen from the at least one host to the at least one vector. By way of example and not limitation, a plurality of vectors that comprise mosquitos may be released into a confined area with a host that comprises a mouse that has received the first pathogen. In some embodiments, the vector may extract a second pathogen from the host that comprises at least one portion of a vaccine or one or more antibodies that may be transferred to at least one secondary host. In some implementations, there may be a predetermined amount of time allotted between the host receiving the first pathogen and the vector extracting the second pathogen to ensure maximum potency of the extracted second pathogen from the host. In some non-limiting exemplary embodiments, the vector may comprise at least one computing device configured to determine when the second pathogen is receivable from the host, such as, for example and not limitation, by determining when a predetermined amount of time has elapsed after the host has received the first pathogen.

In some aspects, at 720, the process 700 may comprise introducing the vector to at least one secondary host, wherein the introduction may facilitate insertion of the second pathogen, via the vector, into the secondary host. In some embodiments, the secondary host may reside in a confined space. In some implementations, a plurality of vectors may comprise two or more living organisms, such as a swarm of infected mosquitoes. In some aspects, the vectors may be rendered incapable of reproducing and released in a concentrated quantity into an open environment where a plurality of secondary hosts reside. In some embodiments, the vector may administer the second pathogen by biting the secondary host or by being consumed by the secondary host, as non-limiting examples. In some aspects, the second pathogen may be administered to the secondary host to prevent the contraction and subsequent transmission or mutation of one or more diseases. In some implementations, by initiating an immune response within the secondary host, the secondary host may develop immunity to the second pathogen, such that subsequent infection of humans through contact, consumption, or other interaction with the secondary host may be substantially prevented.

Referring now to FIG. 8, exemplary method steps for a process 800 for targeted mass inoculation using a transmission system, according to some embodiments of the present disclosure, are illustrated. In some aspects, at 805, at least one host may receive a first at least one pathogen via, for example and not limitation, external injection. In some non-limiting exemplary embodiments, the first pathogen may be transmitted to the host via aerosolized vapor or consumption, as further non-limiting examples of pathogen transmission. In some implementations, at 810, at least one vector may be introduced to the host with the intention of contracting or otherwise receiving a second at least one pathogen, wherein the second pathogen may be the same as the first pathogen, or the second pathogen may comprise one or more at least partially different aspects from the first pathogen. By way of example and not limitation, the second pathogen may comprise one or more antibodies developed by the host in response to the first pathogen. By way of further example and not limitation, a plurality of vectors that comprise drone-based mechanical devices may receive a second pathogen from a mouse that received a first pathogen.

In some implementations, at 815, the vector may receive the second pathogen from the host. In some embodiments, the vector may extract a second pathogen that comprises at least one portion of a vaccine or one or more antibodies that may be transferred to at least one secondary host. In some implementations, there may be a predetermined amount of time allotted between the host receiving the first pathogen and the vector extracting the second pathogen to ensure maximum potency of the extracted second pathogen from the host. In some non-limiting exemplary embodiments, the vector may comprise at least one computing device configured to determine when the second pathogen is receivable from the host, such as, for example and not limitation, by determining when a predetermined amount of time has elapsed after the host has received the first pathogen.

In some aspects, at 820, the vector may be introduced to the secondary host. In some embodiments, the secondary host may reside in a confined space. In some implementations, a plurality of vectors may comprise two or more mechanical devices, such as a plurality of drone-based mechanical devices. In some aspects, the vectors may be released in a concentrated quantity into an open environment where a plurality of secondary hosts reside. In some embodiments, the vectors may administer the second pathogen via direct injection or aerosol disbursement, as non-limiting examples.

In some implementations, at 825, it may be determined whether one or more secondary hosts have previously received the second pathogen. In some aspects, this determination may be facilitated by at least one vector that comprises at least one computing device that comprises at least one indication algorithm that enables the vector to differentiate secondary hosts who have already received the second pathogen from those that have not. In some embodiments, if the vector determines that the secondary host has previously received the second pathogen then, at 830, the vector may select an alternative secondary host to which administer the second pathogen.

In some aspects, at 835, the vector may administer the second pathogen to the secondary host. In some embodiments, the vector may administer the second pathogen via an injection device, as a non-limiting example. In some implementations, the second pathogen may be administered to the secondary host to prevent the contraction and subsequent transmission or mutation of one or more diseases. In some embodiments, by initiating an immune response within the secondary host, the secondary host may develop immunity to the second pathogen, such that subsequent infection of humans through contact, consumption, or other interaction with the secondary host may be substantially prevented.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A transmission system for targeted mass inoculation, comprising:
   a first at least one pathogen;
   at least one host, wherein the first at least one pathogen is administered to the at least one host via external administration, and wherein the at least one host comprises the first at least one pathogen;
   a second at least one pathogen;
   at least one vector, wherein the at least one vector is introduced to the at least one host at a first location, wherein the second at least one pathogen is receivable from the at least one host by the at least one vector, and wherein the at least one vector comprises the second at least one pathogen;

at least one secondary host, wherein the second at least one pathogen is receivable from the at least one vector by the at least one secondary host when the at least one vector is introduced to the at least one secondary host at a second location.

2. The transmission system for targeted mass inoculation of claim 1, wherein the at least one vector comprises at least one computing device, wherein the at least one computing device is configured to identify the at least one secondary host.

3. The transmission system for targeted mass inoculation of claim 2, wherein the at least one computing device is configured to identity the at least one secondary host by executing at least one algorithm.

4. The transmission system for targeted mass inoculation of claim 3, wherein the at least one algorithm is configured to identify the at least one secondary host based on one or more predetermined variables.

5. The transmission system for the targeted mass inoculation of claim 4, wherein at least one of the one or more predetermined variables comprises an identification of whether the at least one secondary host has previously received the second at least one pathogen.

6. The transmission system for targeted mass inoculation of claim 1, wherein the at least one vector comprises at least one unmanned vehicle.

7. The transmission system for targeted mass inoculation of claim 1, wherein the at least one vector comprises at least one aerial vehicle.

8. The transmission system for targeted mass inoculation of claim 1, wherein the at least one vector comprises at least one living organism.

9. The transmission system for targeted mass inoculation of claim 8, wherein the at least one secondary host receives the at least one vector via ingestion.

10. The transmission system for targeted mass inoculation of claim 1, wherein the at least one vector comprises at least one computing device, wherein the at least one vector is configured to determine that the second at least one pathogen is receivable from the at least one host.

11. The transmission system for targeted mass inoculation of claim 10, wherein the second at least one pathogen is receivable after a predetermined amount of time.

12. The transmission system for targeted mass inoculation of claim 1, wherein the second at least one pathogen comprises at least one antibody produced by the at least one host.

* * * * *